United States Patent
Frazee et al.

(10) Patent No.: US 10,245,150 B2
(45) Date of Patent: Apr. 2, 2019

(54) METHOD OF IMPLANTING ASPHERIC HIP BEARING COUPLE

(71) Applicant: DePuy Synthes Products, Inc., Raynham, MA (US)

(72) Inventors: Edmund W. Frazee, Cromwell, IN (US); Craig N. Ernsberger, Granger, IN (US)

(73) Assignee: DePuy Synthes Products, Inc., Raynham, MA (US)

( * ) Notice: Subject to any disclaimer, the term of this patent is extended or adjusted under 35 U.S.C. 154(b) by 1 day.

(21) Appl. No.: 15/486,905

(22) Filed: Apr. 13, 2017

(65) Prior Publication Data
US 2017/0216052 A1    Aug. 3, 2017

Related U.S. Application Data

(62) Division of application No. 14/154,598, filed on Jan. 14, 2014, now Pat. No. 9,668,864, which is a division
(Continued)

(51) Int. Cl.
*A61F 2/32* (2006.01)
*A61F 2/36* (2006.01)
(Continued)

(52) U.S. Cl.
CPC .................. *A61F 2/36* (2013.01); *A61F 2/30* (2013.01); *A61F 2/32* (2013.01); *A61F 2/34* (2013.01);
(Continued)

(58) Field of Classification Search
CPC ............................................ A61F 2002/3623
See application file for complete search history.

(56) References Cited

U.S. PATENT DOCUMENTS

| 3,510,883 A | 5/1970 | Cathcart, III |
| 3,521,302 A | 7/1970 | Müller |

(Continued)

FOREIGN PATENT DOCUMENTS

| DE | 4428290 A1 | 2/1996 |
| DE | 19915814 A1 | 10/2000 |

(Continued)

OTHER PUBLICATIONS

Sbarbaro, Jr., "The Sbarbaro Total Hip," published at least as early as Feb. 4, 2007 (1 page).
(Continued)

*Primary Examiner* — Yashita Sharma
*Assistant Examiner* — Rebecca S Preston
(74) *Attorney, Agent, or Firm* — Maginot, Moore & Beck, LLP (57) ABSTRACT

In one embodiment a method of implanting a prosthetic includes implanting a first member including a concave articulation surface portion defined by a first radius of curvature in a first bone, implanting in a second bone a second member including a first convex articulation surface portion defined by a second radius of curvature and a second convex articulation surface defined by a third radius of curvature, wherein the second convex articulation surface is defined by the lemon portion of a spindle torus and each of the second radius of curvature and the third radius of curvature has a length that is different from the length of the first radius of curvature by less than 0.05 millimeters and wherein the origin of the second radius of curvature is not coincident with the origin of the third radius of curvature, and bringing the first member into slidable contact with the second member.

16 Claims, 7 Drawing Sheets

Related U.S. Application Data of application No. 13/172,693, filed on Jun. 29, 2011, now Pat. No. 8,652,213, which is a division of application No. 12/005,837, filed on Dec. 28, 2007, now Pat. No. 7,985,262.

(51) Int. Cl.

| | | |
|---|---|---|
| *A61F 2/30* | (2006.01) | |
| *A61F 2/40* | (2006.01) | |
| *A61F 2/34* | (2006.01) | |
| *A61F 2/46* | (2006.01) | |
| *A61F 2/28* | (2006.01) | |

(52) U.S. Cl.
CPC .............. *A61F 2/3609* (2013.01); *A61F 2/40* (2013.01); *A61F 2/4607* (2013.01); *A61F 2/4637* (2013.01); *A61F 2002/2828* (2013.01); *A61F 2002/302* (2013.01); *A61F 2002/3065* (2013.01); *A61F 2002/30115* (2013.01); *A61F 2002/30116* (2013.01); *A61F 2002/30327* (2013.01); *A61F 2002/30403* (2013.01); *A61F 2002/30649* (2013.01); *A61F 2002/30655* (2013.01); *A61F 2002/30657* (2013.01); *A61F 2002/30658* (2013.01); *A61F 2002/30935* (2013.01); *A61F 2002/3496* (2013.01); *A61F 2002/3498* (2013.01); *A61F 2002/3623* (2013.01)

(56) References Cited

U.S. PATENT DOCUMENTS

| | | | |
|---|---|---|---|
| 4,031,570 A | 6/1977 | Frey | |
| 4,784,662 A | 11/1988 | Müller | |
| 4,840,632 A | 6/1989 | Kampner | |
| 4,911,723 A | 3/1990 | Menschik | |
| 5,383,936 A | 1/1995 | Kubein-Meesenburg et al. | |
| 5,443,519 A | 8/1995 | Averill et al. | |
| 5,549,690 A | 8/1996 | Hollister et al. | |
| 5,549,693 A | 8/1996 | Roux et al. | |
| 5,609,643 A | 3/1997 | Colleran et al. | |
| 5,641,323 A | 6/1997 | Caldarise | |
| 5,879,405 A | 3/1999 | Ries et al. | |
| 5,879,406 A | 3/1999 | Lilley | |
| 5,904,720 A * | 5/1999 | Farrar ................... | A61L 27/045 623/22.15 |
| 5,928,285 A | 7/1999 | Bigliani et al. | |
| 5,972,032 A | 10/1999 | Lopez et al. | |
| 6,013,103 A | 1/2000 | Kaufman et al. | |
| 6,059,830 A | 5/2000 | Lippincott, III et al. | |
| 6,126,695 A | 10/2000 | Semlitsch | |
| 6,660,040 B2 | 12/2003 | Chan et al. | |
| 6,706,068 B2 | 3/2004 | Ferree | |
| 7,985,262 B2 | 7/2011 | Frazee et al. | |
| 8,652,213 B2 | 2/2014 | Frazee et al. | |
| 2004/0225370 A1 | 11/2004 | Cruchet et al. | |
| 2005/0087047 A1 | 4/2005 | Farrar | |
| 2005/0256584 A1 | 11/2005 | Farrar | |
| 2007/0073410 A1 | 3/2007 | Raugel | |
| 2008/0114459 A1 | 5/2008 | Scott et al. | |
| 2010/0063589 A1 | 3/2010 | Tepic | |

FOREIGN PATENT DOCUMENTS

| | | |
|---|---|---|
| EP | 0226762 A1 | 7/1987 |
| EP | 0302850 A2 | 2/1989 |
| EP | 0648478 A2 | 4/1995 |
| EP | 0681815 A1 | 11/1995 |
| EP | 0841041 A2 | 5/1998 |
| EP | 0748193 B1 | 12/2001 |
| EP | 0841041 B1 | 9/2002 |
| EP | 1337204 A1 | 8/2003 |
| EP | 1340477 A2 | 9/2003 |
| EP | 1442725 A2 | 8/2004 |
| EP | 1337204 B1 | 4/2005 |
| EP | 1598033 A1 | 11/2005 |
| EP | 1465557 B1 | 10/2006 |
| EP | 1767171 A1 | 3/2007 |
| EP | 1952786 A2 | 8/2008 |
| EP | 1767171 B1 | 12/2008 |
| FR | 2134170 A1 | 12/1972 |
| GB | 2260705 A | 4/1998 |
| GB | 2366733 A | 3/2002 |
| WO | 1995023566 | 9/1995 |
| WO | 1997016138 | 5/1997 |
| WO | 2002043626 | 6/2002 |
| WO | 03061532 A1 | 7/2003 |
| WO | 2008015287 | 2/2008 |

OTHER PUBLICATIONS

McKee et al., "The McKee-Farrar Total Hip," published at least as early as Feb. 4, 2007 (1 page).

European Search Report in corresponding EP application (i.e., EP08 25 0408), dated Dec. 29, 2009 (4 pages).

European Search Report in corresponding EP application (i.e., EP 08 25 0408), completed Jun. 6, 2008, (2 pages).

European Search Report in corresponding EP application (i.e., EP 08 17 1397), completed May 11, 2009 (2 pages).

Anderson, Andrew Edward, "Computational Modeling of Hip Joint Mechanics," (Apr. 2007) (unpublished Ph.D. dissertation, The University of Utah), (available on the web at mrl.sci.utah.edu/mrl/papers/Dissertation_AEA.pdf).

Bergmann, G. et al. "Hip Contact Forces and Gait Patterns from Routine Activities", Journal of Biomechanics, (2001), 859-871, vol. 34 (13 pages).

Cilingir et al, "Three-Dimensional Anatomic Finite Element Modeling of Hemi-Arthroplasty of Human Hip Joint," Trends in Biomaterials and Artificial Organs, vol. 21(1), pp. 63-72, 2007, (10 pages).

Hurwitz et al., "A new parametric approach for modeling hip forces during gait," Journal of Biomechanics, 2003, pp. 113-119, vol. 36, Elsevier, USA (7 pages).

McKellop, Ph.D. et al, "In Vivo Wear of 3 Types of Metal on Metal Hip Prostheses During 2 Decades of Use," Clinical orthopaedics and Related Research, No. 329S, pp. S128-S140, © 1996 Lippincott-Raven Publishers, (13 pages).

Morlock et al., "Duration and frequency of every day activities in total hip patients," Journal of Biomechanics, 2001, pp. 873-881, vol. 34, Elsevier, USA (9 pages).

Reinbolt et al., "Determination of patient-specific multi-joint kinematic models through two-level optimization," Journal of Biomechanics, 2005, pp. 621-626, vol. 38, Elsevier, USA (6 pages).

\* cited by examiner

METHOD OF IMPLANTING ASPHERIC HIP BEARING COUPLE

This application is a divisional of prior application Ser. No. 14/154,598, filed Jan. 14, 2014, now U.S. Pat. No. 9,668,864, which issued Jun. 6, 2017, which is a divisional of prior application Ser. No. 13/172,693, filed Jun. 29, 2011, now U.S. Pat. No. 8,652,213 which issued Feb. 18, 2014, which is a divisional of prior application Ser. No. 12/005,837, filed Dec. 28, 2007, now U.S. Pat. No. 7,985,262 which issued Jul. 26, 2011, the disclosures of which are each herein totally incorporated by reference in their entirety.

FIELD

This application relates to the field of prosthetic devices, and particularly joint prostheses comprising head and cup arrangements.

BACKGROUND

A common orthopedic joint prosthesis includes a ball and cup arrangement. For example, hip joints typically comprise a rounded femoral head and an acetabular cup. The rounded femoral head is provided on a stem that is configured to engage the intramedullary cavity of the femur and secure the head on the femur. The rounded femoral head includes a convex surface configured to engage a concave surface on the acetabular cup. The acetabular cup is configured for implantation on the acetabulum of the pelvis. When the rounded femoral head is received within the acetabular cup, a ball and socket joint is provided.

In order to reduce wear between the components of the joint prosthesis, the components are manufactured such that the clearance between the bearing surfaces is minimized. The term "clearance" is often used in reference to a "diametral clearance" of the joint prosthesis. The diametral clearance between bearing surfaces is generally considered to be the difference in the diameter defining the bearing surface of the ball and the diameter defining the bearing surface of the cup.

While minimal diametral clearance between the bearing surfaces is desired, at least two factors limit the reduction of clearances. First, manufacturing tolerances generally limit the extent to which clearances may be reduced. For example, for diametral clearances below the 15-30 micron range, it has been observed that imperfect formation of the femoral head and the acetabular cup contributes to local interferences and small deformations that result in wear.

Second, acetabular cup deformation during implantation into the acetabulum also limits the degree to which clearances may be reduced in a hip joint prosthesis. This deformation generally occurs near the equatorial lip of the acetabular cup. For substantially spherical cup and head arrangements, reduction in clearances near the pole of the head also means reduction in clearances near the equatorial lip. In other words, when the head and the cup of a hip prosthesis are substantially spherical, the small clearances near the pole of the head are also found in the region near the equatorial lip of the cup. Thus, when cup deformation occurs near the equatorial lip in a low clearance spherical design, interference is likely to occur between the equatorial lip of the cup and the ball.

One way to reduce clearance complications resulting from acetabular cup deformation is to provide a conformal region having a small clearance near the center of the primary articulation area of the femoral head, and a peripheral region surrounding the conformal region, wherein the peripheral region has a significantly greater clearance than the conformal region, including a significantly greater clearance near the lip of the cup. With this arrangement, deformations near the equatorial lip of the acetabular cup are less likely to result in obstruction with the femoral head because of the increased clearance near the equatorial lip. Although several of these arrangements have been provided in the past, they have not provided optimal solutions. In particular, many of these arrangements include peripheral regions surrounding the conformal region where the clearances in these peripheral regions quickly diverge from the relatively small clearances in the conformal zone. However, when the clearance in the peripheral region is too great, significant wear may result.

Accordingly, what is needed is a joint prosthesis configured to avoid interference between the ball and cup even if the equatorial region of the cup is deformed during implantation. It would also be advantageous if the clearance between the ball and cup could remain relatively low even in a peripheral region surrounding the conformal region.

SUMMARY

A method of implanting a prosthetic ball and cup joint system in one embodiment includes implanting a first member including a concave articulation surface portion defined by a first radius of curvature in a first bone in a joint, implanting in a second bone in the joint a second member including a first convex articulation surface portion defined by a second radius of curvature and a second convex articulation surface defined by a third radius of curvature, wherein the second convex articulation surface is defined by the lemon portion of a spindle torus and each of the second radius of curvature and the third radius of curvature has a length that is different from the length of the first radius of curvature by less than 0.05 millimeters and wherein the origin of the second radius of curvature is not coincident with the origin of the third radius of curvature, and bringing the first member into slidable contact with the second member.

In one or more embodiments, the spindle torus is formed using a circular origin located on a plane that is perpendicular to an axis extending through the origin of the second radius of curvature and through the center of the second articulation surface.

In one or more embodiments, the difference in length between the first radius of curvature and the second radius of curvature is about 0.015 millimeters and the difference in length between the first radius of curvature and the third radius of curvature is about 0.038 millimeters.

In one or more embodiments the first bone is an acetabulum and the second bone is a femur.

In one embodiment, a method of implanting a prosthetic ball and cup joint system includes implanting in a first bone of a joint a cup including a concave surface defining a cavity, the concave surface defined by at least one radius of curvature (RC), implanting in a second bone of the joint a head including an outer surface and configured to fit at least partially within the cavity, the outer surface including a cap portion defined by a cap radius of curvature (RP) and a toroidal portion located about the cap portion and defined by a toroidal radius of curvature (RT), wherein the cap portion is configured to conform with the concave cup surface and the RC is less than 0.05 millimeters longer than the RT, and bringing the head into slidable contact with the cup.

In one or more embodiments, the the toroidal portion is the lemon portion of a spindle torus.

In one or more embodiments the RC is less than 0.05 millimeters longer than the RP.

In one or more embodiments the RP defines the cap portion from a single origin, and the RT has a circular origin located on a plane that is perpendicular to an axis extending through the origin of the second radius of curvature and through the center of the cap portion, the plane located between the origin and the cap portion.

In one or more embodiments the cap portion is defined by an opening angle of less than 125 degrees.

In one or more embodiments the cap portion is defined by an opening angle of about 95 degrees.

In one embodiment, a method of implanting a prosthetic ball and cup joint system, includes implanting in a first bone a cup including a concave surface defining a cavity, the concave surface defined by at least one radius of curvature (RC), implanting in a second bone a head including an articulation portion configured to fit at least partially within the cavity, the articulation portion including a toroidal portion defined by a toroidal radius of curvature (RT) having a circular origin and a cap portion defined by a cap radius of curvature (RP), wherein the RC is less than 0.05 millimeters longer than the RT, and bringing the head into slidable contact with the cup.

In one or more embodiments the circular origin is located on a plane that is perpendicular to an axis extending through the origin of the second radius of curvature and through the center of the cap portion, the plane located between the origin and the cap portion.

The above described features and advantages, as well as others, will become more readily apparent to those of ordinary skill in the art by reference to the following detailed description and accompanying drawings.

DESCRIPTION

Figure 1:
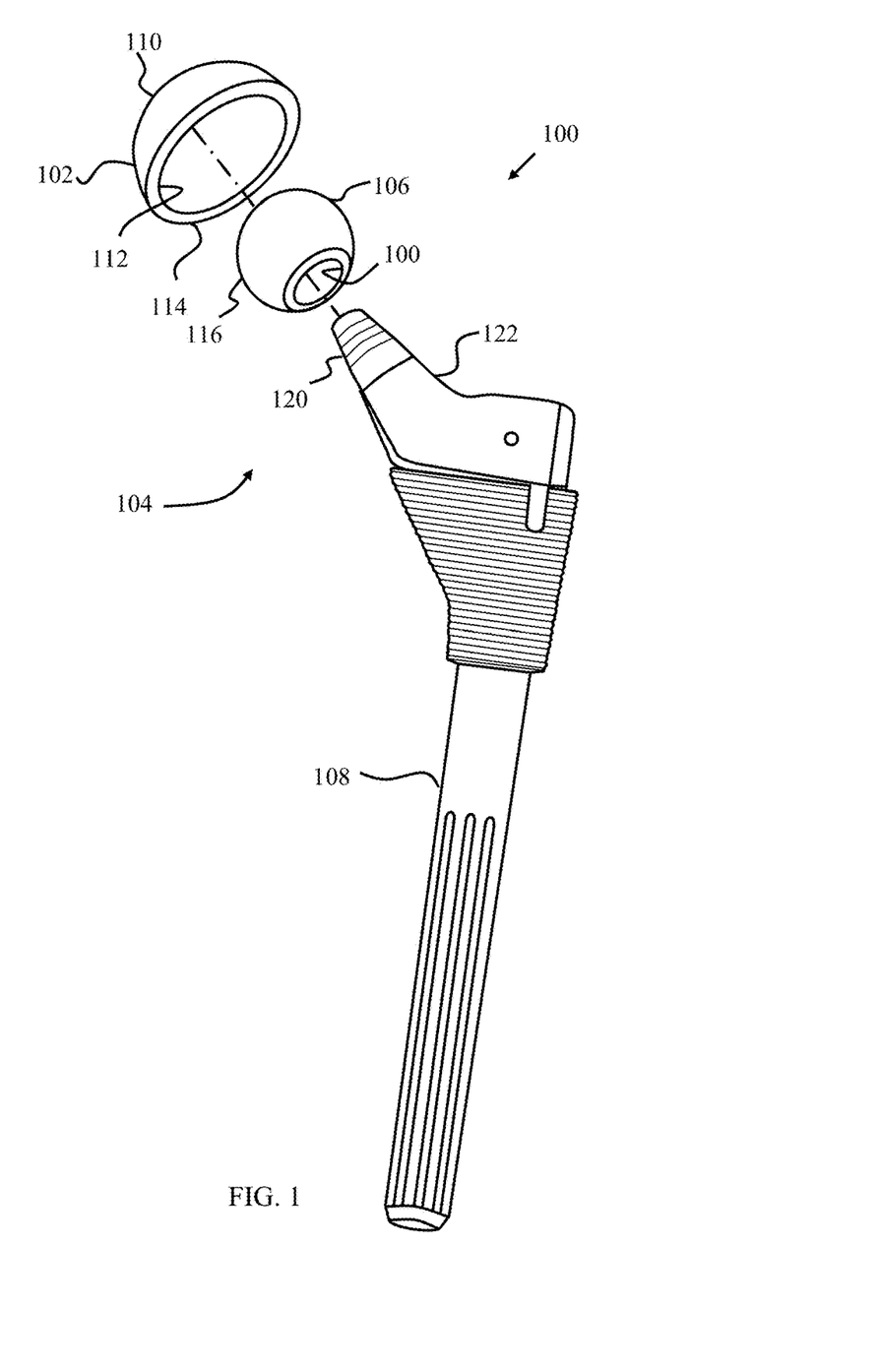
FIG. 1 shows a perspective view of various components of a hip prosthesis including an acetabular cup, a femoral head, and a femoral stem in accordance with principles of the invention.

With reference to FIG. 1, a prosthetic device in the form of a prosthetic hip joint 100 is shown in a disassembled configuration. The prosthetic hip joint 100 includes an acetabular cup 102 and a femoral component 104. The femoral component 104 includes a femoral head 106 (or "ball"), and a femoral stem 108. The femoral head 106 is configured for attachment to the femoral stem 108. The femoral head 106 is also configured to slideably engage the acetabular cup 102.

The acetabular cup 102 is the part of the prosthetic hip joint 100 that forms the socket of a ball-and-socket structure. The acetabular cup 102 includes a convex outer surface 110 configured for engagement with a patient's acetabulum and a concave interior surface 112 configured to engage the femoral head 106. The cup 102 includes a lip 114 which defines a rim in a peripheral region and which extends between the convex outer surface 110 and the concave interior surface 112.

The convex outer surface 110 of the acetabular cup 102 may be provided as part of a shell including a biocompatible material. In at least one embodiment, the shell is comprised of a relatively rigid material, such as a biocompatible metal or ceramic. For example, the shell may be comprised of titanium or cobalt chrome. The concave interior surface 112 of the cup 102 may be in the form of a liner that provides a bearing surface for the acetabular cup 102. The liner may be comprised of a biocompatible material that offers a low coefficient of friction, such as polyethylene. Alternatively, the liner may be comprised of a metal or ceramic. While exemplary materials for the acetabular cup 102 have been offered herein, one of skill in the art will recognize that numerous other biocompatible materials may be used as are known in the art.

The femoral component 104 is used to replace the natural head of a femur. To this end, the femoral head 106 includes a generally ball-shaped outer surface 116 designed and dimensioned to be received at least partially within the cavity defined by the concave interior surface 112 of the acetabular cup 102. The femoral head 106 includes a generally conical bore 118 which is used to fix femoral head 106 to a Morse taper 120 on the neck 122 which extends from the femoral stem 108. The femoral component 104 is comprised of a relatively rigid biocompatible material such as a ceramic or metal. For example, the ball 106 may be comprised of cobalt chrome or stainless steel. While exemplary materials for the femoral component 104 have been offered herein, one of skill in the art will recognize that numerous other biocompatible materials may be used as are known in the art.

Figure 2:
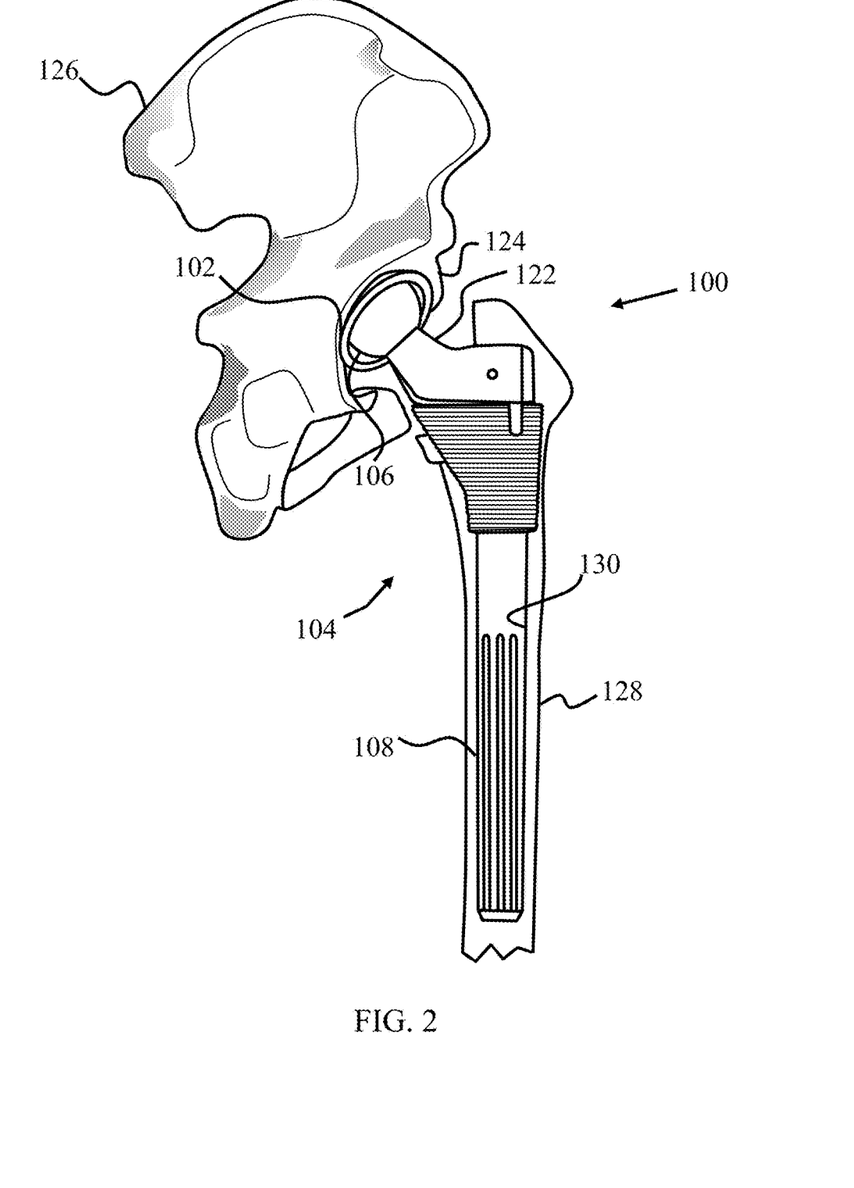
FIG. 2 shows a cutaway view of the hip prosthesis of FIG. 1 assembled and implanted in a pelvis and femur.

As shown in FIG. 2, the prosthetic hip joint 100 may be implanted in a patient by securing the acetabular cup 102 in the acetabulum 124 of the pelvis 126. Also, the femoral component 104 is secured to the femur 128 by inserting the femoral stem 108 within the intramedullary cavity 130 of the femur 128. The femoral head 106 which extends from the neck 122 is brought into slideable contact with the acetabular cup 102 such that the femoral head 106 is allowed to articulate within the acetabular cup 102. This slideable relationship provides for a ball and socket type joint.

Figure 3:
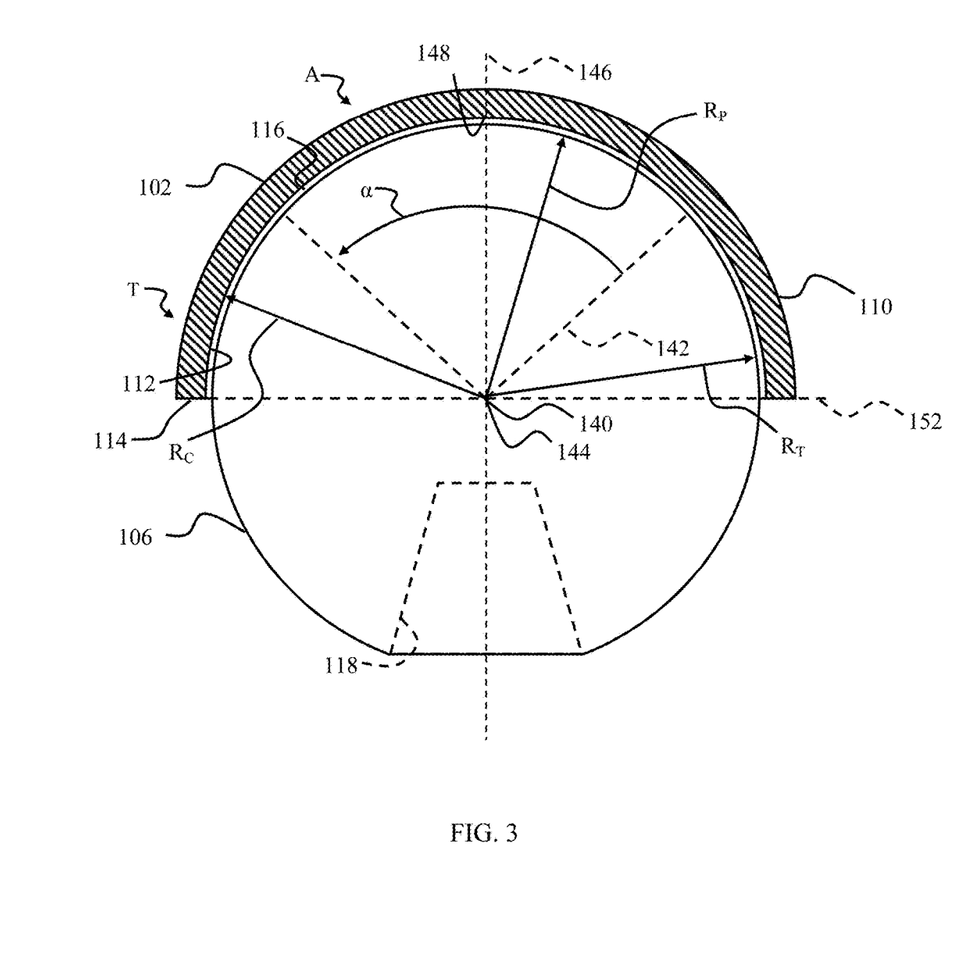
FIG. 3 shows a cross-sectional view of the femoral head and acetabular cup of FIG. 1.

An enlarged cutaway view of the acetabular cup 102 showing the femoral head 106, with the head 106 slightly removed from engagement with the cup 102 is shown in FIG. 3. The configuration of the head 106 defines different zones or regions for the prosthesis, including a primary contact zone A and a toroidal zone T.

The term "primary contact zone" refers to a region of the head 106 which provides the main contact area between the head 106 and the cup 102 for most joint movements once implanted in a patient. Accordingly, with reference to FIG. 3, the convex bearing surface 116 of the head 106 primarily articulates with the concave bearing surface 112 of the cup 102 within the primary contact zone A. Some contact, however, occurs between the head 106 and the cup 102 within the toroidal zone T, particularly with certain extraordinary movements by the patient.

The primary contact zone A is shown as lying within the region subtended by the angle α having a vertex at an origin 140 of the spherical cap portion. This means that the primary contact zone A is provided within a perimeter defined by the intersection of a cone 142 with the convex outer surface 116 of the head 106, the cone 142 having an apex 144 at the origin 140 and an aperture (or "opening angle") of α. As shown in FIG. 3, the cone 142 is symmetric about an axis 146 extending through the origin 140. The toroidal zone T extends from the primary contact zone A to the conical bore 118.

Studies such as *Bergmann*, et al., "Hip contact forces and gait patterns from routine activities," J. Biomech., 2001, 34(7), 859-871, have shown that contact predominantly occurs in an area defined by opening angles between 85 and 145 degrees. Accordingly, while the α in this embodiment is 95 degrees other opening angles between 85 and 145 degrees may be used. Selection of opening angles between 95 and 125 degrees provide for good radial clearance which is discussed below.

The acetabular cup 102 is shown in FIG. 3 centered upon and symmetric with respect to an apex 148, which is the deepest portion of the cup 102, in the coronal plane. In particular, the apex 148 of the concave bearing surface 112 of the cup 102 is shown in FIG. 3 aligned with the axis 146. When the cup 102 is in this position relative to the head 106, it is considered to be in a centered position. In practice, the cup 102 and head 106 are generally aligned in the implanted position such that the apex 148 of the cup 102 is about thirty degrees off the axis 146 of the head 106 in the coronal plane and about fifteen degrees off the axis 146 of the head 106 in the sagittal plane. For a spherical cup geometry, the articulation area on the head is independent of the cup orientation.

Figure 4:
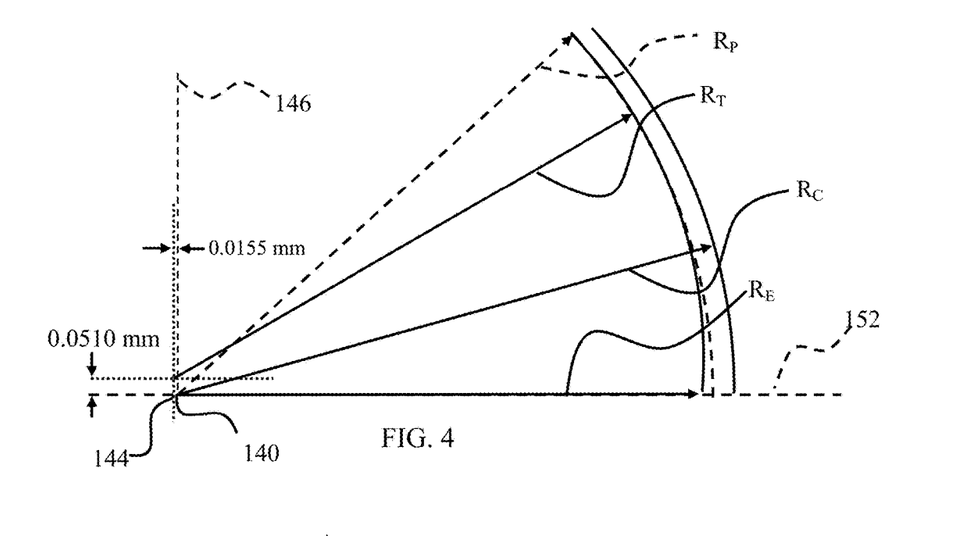
FIG. 4 shows a diagrammatic representation of the radii which define the inner surface of the cup, a primary contact zone and a toroidal zone in accordance with principles of the invention.

With continued reference to FIG. 3, the outer surface 116 of the head 106 at any given point is defined by a radius of curvature ($R_H$). The head 106 does not form a perfect sphere, however, and the radius of curvature $R_H$ is different at different points on the surface 116 of the head 106 as shown in FIG. 4. The radius of curvature in the primary contact zone ($R_P$) in the embodiment of FIG. 3 is 18.035 mm, while the radius of curvature in the toroidal zone ($R_T$) is 18.0120 mm.

Figure 5:
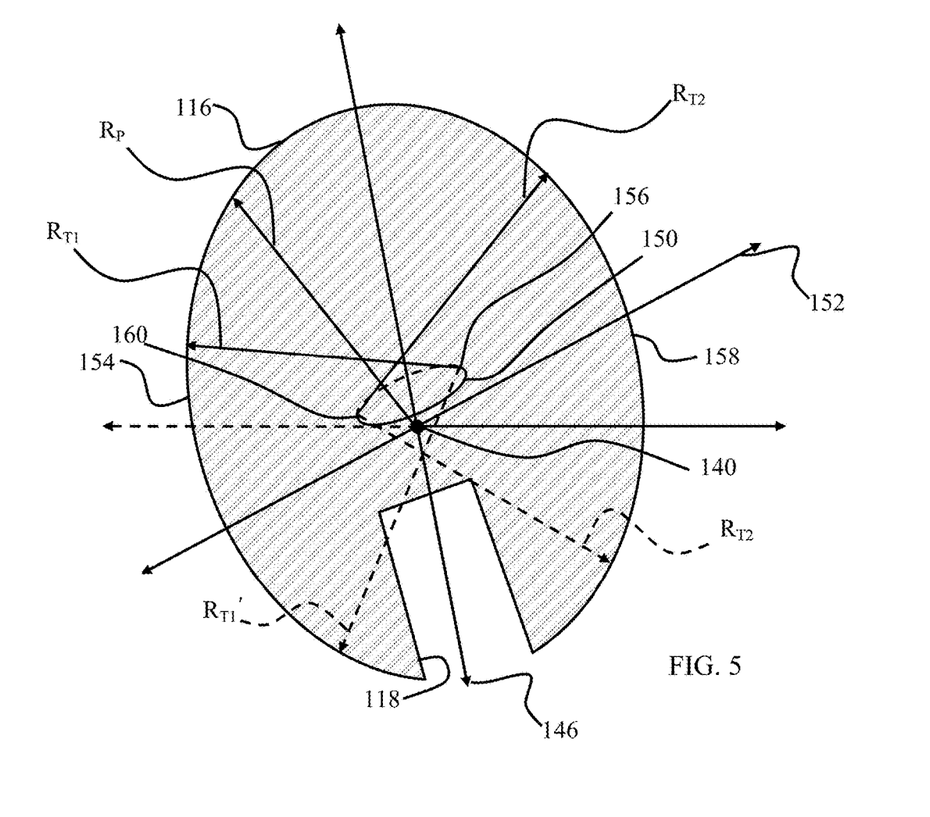
FIG. 5 depicts a perspective view of a slice of the femoral head of FIG. 3 showing the relative positions of the origin for the radius of curvature of the cap portion of the femoral head and the circular origin of the radius of curvature of the toroidal section.

Moreover, as shown in FIG. 4, the origin of the $R_P$ is located at the origin 140. The origin of the $R_T$, however, is defined by a circle 150 shown in FIG. 5. FIG. 5 depicts a slice of the femoral head 106 taken along the plane defined by the axis 146 and an axis 152 which is perpendicular to the axis 146 and which intersects the origin 140. The portion of the circle 150 which is behind the slice of the ball 106 as depicted in FIG. 5 is shown as a dashed line. The circle 150 has a radius of 0.0155 mm and lies within a plane that is located 0.0510 mm above the origin 140 and positioned perpendicular to the axis 152.

Any given point on the outer surface 116 in the toroidal zone T is defined by an $R_T$ having an origin located on the point of the circle 150 farthest away from the point being defined. For example, the arc 154 of the surface 116 shown in FIG. 5 is defined by sweeping $R_T$ from the position shown as $R_{T1}$ to the position of $R_{T1}'$ while maintaining the origin of the $R_T$ at the point 156. Similarly, the arc 158 of the surface 116 of FIG. 5 is defined by sweeping $R_T$ from the position shown as $R_{T2}$ to the position of $R_{T2}'$ while maintaining the origin of the $R_T$ at the point 160. Thus, the origin of the $R_T$ shown in FIG. 4 is located at a point 0.0510 mm above the axis 152 and 0.0155 to the left of the axis 146.

Figure 6:
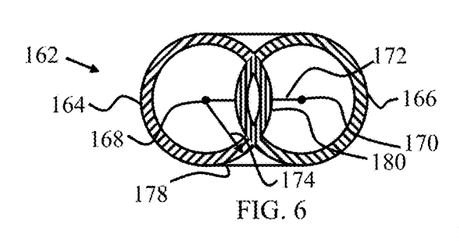
FIG. 6 shows a cross sectional view of a spindle torus.
Figure 7:
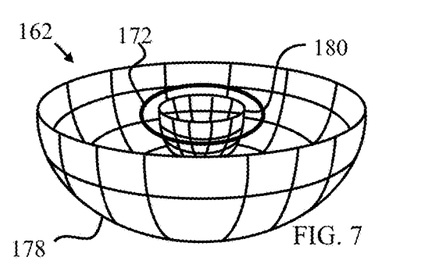
FIG. 7 shows a three-dimensional representation of the bottom half of the torus of FIG. 6 including the apple shaped or outer surface and the lemon shaped or inner surface of the torus.

From a mathematical construct, the toroidal zone T is thus formed as the lemon of a spindle torus. A spindle torus is formed by the revolution of a circle about an axis coplanar with the circle. A cross sectional view of a torus 162 is shown in FIG. 6 while FIG. 7 is a three-dimensional representation of the bottom half of the torus 162. The torus 162 in cross-section presents two overlapping circles 164 and 166. The centers 168 and 170 of the circles 164 and 166 are points on a circle 172. The circle 172 is thus the circular origin of the torus 162 having a radius of curvature 174 which is the radius of the circles 164 and 166. The outer surface 178 of the torus is referred to as the "apple" shape while the inner surface 180 is referred to as the "lemon" shape.

Figures 8, 9, 10:
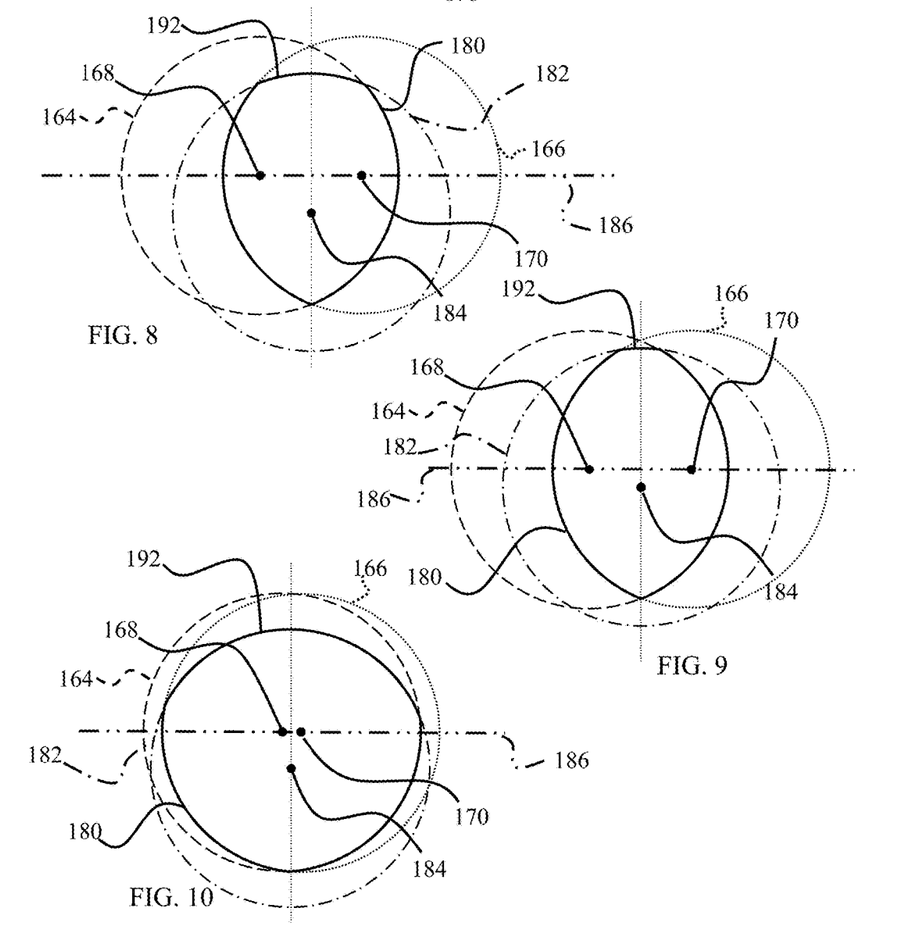
FIG. 8 shows a diagrammatic representation of the definition of the outer surface of a femoral ball using the lemon shape or inner surface of a spindle torus and an arc of a circle centered below the axis defined by the center of the circle (the circular origin) which defines the spindle torus.
FIG. 9 shows a diagrammatic representation of the circles of FIG. 8 with the center of the circle used to define the arc or cap portion closer to the axis defined by the center of the circle (the circular origin) thereby decreasing the size of the cap portion as compared with FIG. 8.
FIG. 10 shows a diagrammatic representation of the circles of FIG. 8 with the center of the circle used to define the arc or cap portion at the same distance away from the axis defined by the center of the circle (the circular origin) as shown in FIG. 8 but with the diameter of the circular origin reduced (i.e. the apple shaped portion is more circular) thereby increasing the size of the cap portion as compared with FIG. 8.

As shown in FIG. 8, the lemon 180 and a circle 182 having a center 184 located below the axis 186 defined by the centers 168 and 170 of the circles 164 and 166, respectively can be used to define a cap 192. FIG. 9 is identical to FIG. 8 with the exception that the origin 184 of the circle 182 has been positioned closer to the axis 186 defined by the circular origin of the outer surface 178. As is apparent from comparing FIG. 9 with FIG. 8, as the origin 184 of the circle 182 approaches the axis 186, the cap portion 192 becomes smaller. The shape can be further modified by moving the origin 184 closer to one or the other of the centers 168 and 170. Consequently, the location and extent of the discontinuity between the cap portion 192 and the outer surface 180 can be modified.

Thus, by moving the origin or center 184 closer to the axis defined by the circular origin, the spherical cap portion 192 becomes smaller. For example, given a circular origin diameter of 0.031 millimeters, an $R_P$ of 18.035 millimeters and an $R_T$ of 18.0120 millimeters, a cap portion with a 95 degree opening angle is obtained by positioning the origin of the spherical cap portion 0.051 millimeters below the plane of the circular origin. In the event a cap portion with a 125 degree opening angle is desired using the same radii, one need only position the origin of the spherical cap portion at about 0.08 millimeters below the plane of the circular origin.

FIG. 10 is identical to FIG. 8 with the exception that the diameter of the circular origin 172 of the outer surface 178 is reduced. Thus, two centers 168 and 170 of the circles 164 and 166 are positioned more closely together. As is apparent from comparing FIG. 10 with FIG. 8, as the two centers 168 and 170 of the circles 164 and 166 converge, that is, as the diameter of the circular origin 172 is shortened, the shape of the inner surface 180 becomes more circular, thereby increasing the size of the cap portion 192. Consequently, the location and extent of the discontinuity between the cap portion 192 and the outer surface 180 can be modified.

Moreover, while the circles 164, 166 and 182 are shown with identical radii, the radius of the circle 182 may be shorter or longer than the radii of the circles 164 and 166 in certain embodiments. Similarly, the radius of the circle 182 may be the same, shorter or longer than the radius or radii of a particular cup.

Returning to FIG. 3, the acetabular cup 102 is defined by a radius of curvature ($R_C$). The $R_C$ extends from the virtual center of the cup 102, which as depicted in FIG. 3 is coincident with the origin 140, to the concave inner surface 112 of the acetabular cup 102. The $R_C$ is constant for all points on the concave inner surface 112 such that the concave inner surface 112 of the cup forms a hemisphere. The $R_C$ in this embodiment is 18.050 mm.

The radial clearance ($R_{CL}$) or difference between $R_C$ and $R_H$ at a given point on the head 106 and the opposing point on the cup 102 (i.e., on a given ray extending from the origin 140 of the head 106 to the concave surface 112 of the cup 102) does not necessarily translate directly into a spatial clearance between the head 106 and the cup 102. For example, when the prosthesis 100 is implanted and the head 106 is in a centered position, the head 106 is in contact with the cup 102, even though the $R_{CL}$ is 0.015 mm ($R_C$ (18.050 mm)–$R_P$ (18.035 mm)). The value of $R_{CL}$, however, is useful in quantifying the conformity between the surface of the ball 106 and the cup 102 which are in contact. For example, a small $R_{CL}$ for a given contact area, i.e. less than 0.05 mm, generally provides lower wear rates. Accordingly, the prosthetic hip joint 100 maintains an $R_{CL}$ less than 0.050 mm throughout the primary contact zone A.

Additionally, the toroidal zone T provides increased clearance between the ball 106 and the cup 102 at the lip 114. With reference to the embodiment of FIG. 3, the acetabular cup 102 is exactly hemispherical. Thus, the width of the cup 102 at the plane defined by the lip 114 is the widest portion of the cup 102. Accordingly, when the ball 106 is centered within the cup 102 and in contact with the cup 102 along the axis 146, the origin 140 is located 0.015 mm above the plane defined by the lip 114. Thus, the widest diameter defined by the toroidal zone T will be located on a plane positioned 0.066 mm above the plane defined by the lip 114. At this location, the width of the toroidal zone is 35.993 mm. The width of the cup 102 on a plane located 0.066 mm above the plane defined by the lip 114 is 36.0998 mm. Thus, the clearance is 0.1068 mm.

At the plane defined by the lip 114, however, the width of the toroidal zone T decreases to 35.9927 mm while the width of the cup increases to 36.1 mm resulting in a clearance of 0.1073 mm. In contrast, a precisely circular ball with a radius of 18.035 mm would result in a clearance at the plane defined by the lip 114 of 0.0300 mm.

Figure 11:
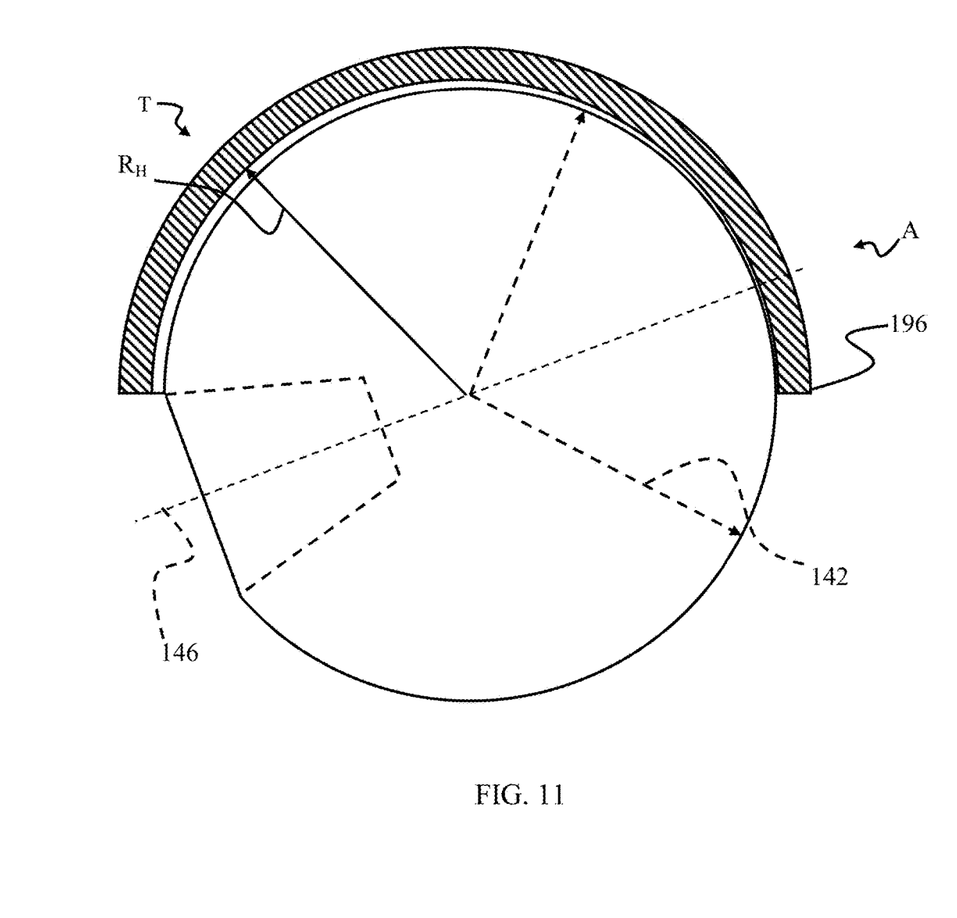
FIG. 11 shows a cross-sectional view of the femoral head and acetabular cup of FIG. 1 with the femoral head rotated within the acetabular cup and contacting the acetabular cup at the opening of the acetabular cup.

Referring to FIG. 11, the femoral ball 106 is rotated within the acetabular cup 102 to the maximum amount possible before dislocation would occur in an implanted device. The contact area between the ball 106 and the cup 102 for purposes of this example is centered at location 196. This configuration, which is not a normally occurring configuration, provides insight into the smallest expected clearance for the embodiment of FIG. 3. That is, as the contact area is located more fully within the cup 102 with the ball 106 rotated as shown in FIG. 6, the origin 140 of the spherical cap portion moves off of the plane defined by the lip 114, thereby increasing the clearance at the lip 114. The width of the ball 106 in the plane defined by the lip 114 in the configuration of FIG. 6 is 36.04699 mm resulting in a clearance of 0.0530 mm. In contrast, a precisely circular ball with a radius of 18.035 mm in the configuration of FIG. 6 would result in a clearance at the plane defined by the lip 114 of 0.0300 mm.

Thus, while the configuration of the prosthetic hip joint 100 provides the desired conformity between the ball 106 and the cup 102 regardless of the orientation of the ball 106 within the cup 102, the conformity is achieved while providing increased clearance on the plane defined by the lip 114.

Figure 12:
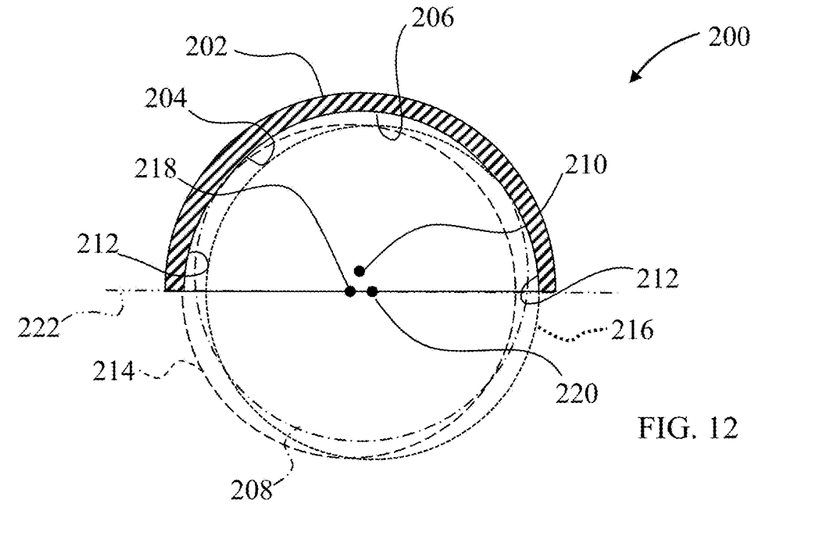
FIG. 12 shows a cross-sectional view of an alternative embodiment of an acetabular cup with a diagrammatic overlay showing the use of a toroidal surface within the acetabular cup in accordance with principles of the invention.

An alternative embodiment of an acetabular cup 200 is shown in FIG. 12. The acetabular cup 200 includes an outer surface 202 and an inner surface 204. The inner surface 204 includes a cap portion 206 formed on a circle 208 with a center 210 and a toroidal portion 212. The toroidal portion 212 is shown in cross-section as formed on two circles 214 and 216 having centers 218 and 220, respectively. The center 208 is located above the axis 222 defined by the centers 218 and 220. In this embodiment, the toroidal portion 212 is formed on the apple or outer surface of the torus defined by the rotation of the circles 214 and 216. Accordingly, even if each of the circles 208, 214 and 216 have the same diameter, the diameter of the cup 200 in the toroidal portion 212 will be greater than the diameter in the cap portion 206.

Figure 13:
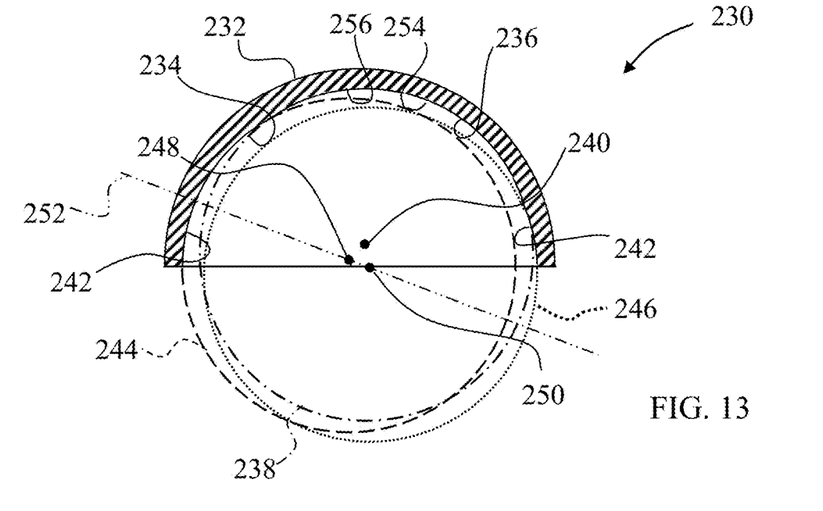
FIG. 13 shows a cross-sectional view of an alternative embodiment of an acetabular cup with a diagrammatic overlay showing the use of a toroidal surface within the acetabular cup wherein the cap portion and toroidal portion of the acetabular cup are not centered within the acetabular cup in accordance with principles of the invention.

As noted above, a cup and head are generally aligned in the implanted position such that the apex of the cup is about thirty degrees off the axis of the head in the coronal plane and about fifteen degrees off the axis of the head in the sagittal plane. Accordingly, it may be desired to modify the location of the cap portion of a cup. For example, FIG. 13 shows an acetabular cup 230 includes an outer surface 232 and an inner surface 234. The inner surface 234 includes a cap portion 236 formed on a circle 238 with a center 240 and a toroidal portion 242. The toroidal portion 242 is shown in cross-section section as formed on two circles 244 and 246 having centers 248 and 250, respectively. The center 238 is located above the axis 252 defined by the centers 248 and 250.

In this embodiment, the toroidal portion 242 is formed on the apple or outer surface of the torus defined by the rotation of the circles 244 and 246. Accordingly, even if each of the circles 238, 244 and 246 have the same diameter, the diameter of the cup 230 in the toroidal portion 242 will be greater than the diameter in the cap portion 236. Additionally, the cap portion 236 is centered at a location 254 which is offset from the apex 256 or deepest portion of the cup 230. Thus, the cap portion 236 is centered on the normal contact area between a ball and the cup 230 when the ball and cup 230 are implanted. Accordingly, most of the contact between a ball and the cup 236 when implanted will occur within the cap portion 236.

Although the present invention has been described with respect to certain preferred embodiments, it will be appreciated by those of skill in the art that other implementations and adaptations are possible. Moreover, there are advantages to individual advancements described herein that may be obtained without incorporating other aspects described above. Therefore, the spirit and scope of the appended claims should not be limited to the description of the preferred embodiments contained herein.

What is claimed is:

1. A method of implanting a prosthetic ball and cup joint system, comprising:
    implanting a first member including a concave articulation surface portion defined by a first radius of curvature in a first bone in a joint;
    implanting in a second bone in the joint a second member including a first convex articulation surface portion defined by a second radius of curvature and a second convex articulation surface defined by a third radius of curvature, wherein the second convex articulation surface is defined by the lemon portion of a spindle torus and each of the second radius of curvature and the third radius of curvature has a length that is different from the length of the first radius of curvature by less than 0.05 millimeters and wherein the origin of the second radius of curvature is not coincident with the origin of the third radius of curvature; and
    bringing the first member into slidable contact with the second member.

2. The method of claim 1, wherein the spindle torus is formed using a circular origin located on a plane, wherein the plane is perpendicular to an axis, the axis extending through the origin of the second radius of curvature and through the center of the second articulation surface.

3. The method of claim 2, wherein the difference in length between the first radius of curvature and the second radius of curvature is about 0.015 millimeters and the difference in length between the first radius of curvature and the third radius of curvature is about 0.038 millimeters.

4. The method of claim 1, wherein the first bone is an acetabulum and the second bone is a femur.

5. A method of implanting a prosthetic ball and cup joint system, comprising:
    implanting in a first bone of a joint a cup including a concave surface defining a cavity, the concave surface defined by at least one radius of curvature (RC);
    implanting in a second bone of the joint a head including an outer surface, the outer surface including a cap portion defined by a cap radius of curvature (RP) and a toroidal portion located about the cap portion and defined by a toroidal radius of curvature (RT), wherein the RC is less than 0.05 millimeters longer than the RT and the RT has a circular origin; and
    bringing the head into slidable contact with the cup by at least partially inserting the head into the cavity.

6. The method of claim 5, wherein the toroidal portion is the lemon portion of a spindle torus.

7. The method of claim 5, wherein the RC is less than 0.05 millimeters longer than the RP.

8. The method of claim 7, wherein:
    the RP defines the cap portion from a single origin; and
    the circular origin is located on a plane that is perpendicular to an axis extending through the single origin of the cap portion and through the center of the cap portion, the plane located between the single origin and the cap portion.

9. The method of claim 8, wherein the cap portion is defined by an opening angle of less than 125 degrees.

10. The method of claim 9, wherein the cap portion is defined by an opening angle of about 95 degrees.

11. The method of claim 5, wherein the first bone is an acetabulum and the second bone is a femur.

12. A method of implanting a prosthetic ball and cup joint system, comprising:
    implanting in a first bone a cup including a concave surface defining a cavity, the concave surface defined by at least one radius of curvature (RC);
    implanting in a second bone a head including an articulation portion, the articulation portion including a toroidal portion defined by a toroidal radius of curvature (RT) having a circular origin and a cap portion defined by a cap radius of curvature (RP), wherein the RC is less than 0.05 millimeters longer than the RT; and
    bringing the head into slidable contact with the cup by at least partially inserting the head into the cavity.

13. The method of claim 12, wherein the circular origin is located on a plane that is perpendicular to an axis extending through an origin of the RP and through the center of the cap portion, the plane located between the origin and the cap portion.

14. The method of claim 13, wherein the cap portion is defined by an opening angle of less than 125 degrees.

15. The method of claim 14, wherein the cap portion is defined by an opening angle of about 95 degrees.

16. The method of claim 12, wherein the first bone is an acetabulum and the second bone is a femur.

* * * * *